United States Patent [19]

Wiesehahn et al.

[11] Patent Number: 5,106,619
[45] Date of Patent: Apr. 21, 1992

[54] PREPARATION OF INACTIVATED VIRAL VACCINES

[75] Inventors: Gary P. Wiesehahn, Alameda; Richard P. Creagan, Alta Loma; David R. Stevens, Fremont; Richard Giles, Alameda, all of Calif.

[73] Assignee: Diamond Scientific Co., Des Moines, Iowa

[21] Appl. No.: 463,081

[22] Filed: Jan. 10, 1990

Related U.S. Application Data

[60] Continuation of Ser. No. 69,117, Jul. 2, 1987, abandoned, which is a division of Ser. No. 785,354, Oct. 7, 1985, Pat. No. 4,693,981, which is a continuation-in-part of Ser. No. 592,661, Mar. 23, 1984, Pat. No. 4,556,556, which is a continuation-in-part of Ser. No. 563,939, Dec. 20, 1983, Pat. No. 4,545,987.

[51] Int. Cl.$^5$ .......................... A61K 39/12; C12N 7/04
[52] U.S. Cl. ........................................ 424/89; 424/90; 435/236; 435/238; 546/270
[58] Field of Search .................... 424/89, 90; 435/236, 435/238; 546/270

[56] References Cited

U.S. PATENT DOCUMENTS 4,036,952 7/1977 Bauer et al. ........................ 424/89

Primary Examiner—Johnnie R. Brown
Assistant Examiner—Abdel A. Mohamed
Attorney, Agent, or Firm—Joseph C. Gil; Lyndanne M. Whalen

[57] ABSTRACT

Vaccines employing inactivated viruses having improved retention of antigenic characteristics are prepared by psoralen-inactivation of the live virus in a non-oxidizing atmosphere. By excluding oxygen and other oxidizing species from the inactivation medium, degradation of the antigen characteristics resulting from irradiation with ultraviolet light is largely prevented. The resulting inactivated viruses are employed in vaccine preparations for the inoculation of susceptible hosts to inhibit viral infection.

12 Claims, No Drawings

PREPARATION OF INACTIVATED VIRAL VACCINES

This application is a continuation of application Ser. No. 07/069,117, filed Jul. 2, 1987, now abandoned, which is a divisional of Ser. No. 06/785,354, filed Oct. 7, 1985 (U.S. Pat. No. 4,693,981), which is a continuation-in-part of Ser. No. 06/592,661, filed Mar. 23, 1984 (U.S. Pat. No. 4,556,556), which is a continuation-in-part of Ser. No. 06/563,939, filed Dec. 20, 1983 (U.S. Pat. No. 4,545,987).

BACKGROUND OF THE INVENTION

1. Field of the Invention

The present invention relates to the preparation of inactivated viral vaccines. More particularly, the invention relates to psoralen inactivation of viral particles under conditions which limit antigenic degradation of the viral particles caused by the inactivation.

Vaccination against both bacterial and viral diseases has been one of the major accomplishments of medicine over the past century. While effective vaccines have been developed for a large number of diseases, development of safe and effective vaccines for a number of other diseases remains problematic. The use of inactivated or killed microbial agents as a vaccine, although generally safe, will not always be effective if the immunogenic characteristics of the agent are altered. Indeed, the preferential degradation of certain antigens on the inactivated microorganisms might produce an immune response which allows for an immunopathological response when the host is later challenged with the live microorganism. In contrast, the preparation of live, attenuated microbial agents as a vaccine will often provide improved immunologic reactivity, but increases the risk that the vaccine itself will be infectious, e.g., as a result of reversion, and that the organism will be able to propagate and provide a reservoir for future infection.

Thus, one must generally choose between improved effectiveness and greater degree of safety when selecting between the viral inactivation and viral attenuation techniques for vaccine preparation. The choice is particularly difficult when the virus is resistant to inactivation and requires highly rigorous inactivation conditions which are likely to degrade the antigenic characteristics.

It is therefore desirable to provide improved methods for inactivating viruses, which methods are capable of inactivating even the most resistant viruses under conditions which do not substantially degrade the antigenic structure of the viral particles. In particular, the inactivated viruses should be useful as vaccines and free from adverse side effects at the time of administration as well as upon subsequent challenge with the live virus.

2. Description of the Prior Art

The reactivity of psoralen derivatives with viruses has been studied. See, Hearst and Thiry (1977) Nuc. Acids Res. 4:1339-1347; and Talib and Banerjee (1982) Virology 118:430-438. U.S. Pat. Nos. 4,124,598 and 4,196,281 to Hearst et al. suggest the use of psoralen derivatives to inactivate RNA viruses, but include no discussion of the suitability of such inactivated viruses as vaccines. U.S. Pat. No. 4,169,204 to Hearst et al. suggests that psoralens may provide a means for inactivating viruses for the purpose of vaccine production but presents no experimental support for this proposition. European patent application 0 066 886 by Kronenberg teaches the use of psoralen inactivated cells, such as virus-infected mammalian cells, for use as immunological reagents and vaccines. Hanson (1983) in: Medical Virology II, de la Maza and Peterson, eds., Elsevier Biomedical, New York, pp. 45-79, reports studies which have suggested that oxidative photoreactions between psoralens and proteins may occur.

SUMMARY OF THE INVENTION

The present invention provides for the production of furocoumarin-inactivated viral vaccines under conditions which substantially preserve the antigenic characteristics of the inactivated viral particles. It has been recognized by the inventors herein that the inactivation of viruses by exposure to ultraviolet radiation in the presence of furocoumarin compounds can degrade the antigenic structure of the viral particle. While such degradation can be limited by employing less rigorous inactivation conditions, certain recalcitrant viruses require relatively harsh inactivation conditions in order to assure that all residual infectivity is eliminated. The inactivation condition required to eliminate substantially all infectivity in such recalcitrant viruses can so degrade the viral particle that it is unsuitable for use as the immunogenic substance in a vaccine. Even if the degradation is not so complete, partial degradation of the antigenic characteristics may render the vaccine less effective than would be desirable. That is, the vaccine may require higher concentrations of the inactivated viral particles in each inoculation, and/or the vaccination program may require additional inoculations in order to achieve immunity.

According to the present invention, vaccines are prepared by treatment with furocoumarins and long wavelength ultraviolet (UVA) light under conditions which limit the availability of oxygen and other reactive, particularly oxidizing, species. It has been found that such conditions allow for the inactivation of even recalcitrant viral particles without substantial degradation of the antigenic characteristics of those particles. Thus, viruses which have heretofore been resistant to furocoumarin-inactivation may now be inactivated without loss of the desired immunogenicity, and viruses which have previously been successfully inactivated may now be inactivated under conditions which better preserve their antigenic characteristics, making them more efficient immunogenic substances for use in vaccines.

DESCRIPTION OF THE SPECIFIC EMBODIMENTS

According to the present invention, vaccines useful for the inoculation of mammalian hosts, including both animals and humans, against viral infection are provided. The vaccines are prepared by inactivation of live virus in an inactivation medium containing an amount of an inactivating furocoumarin sufficient to inactivate the virus upon subsequent irradiation with long wavelength ultraviolet radiation. Degradation of the antigenic characteristics of the live virus is reduced or eliminated by limiting the availability of oxygen and other oxidizing species in the inactivation medium. Suitable vaccines may be prepared by combining the inactivated viruses with a physiologically-acceptable carrier, typically an adjuvant, in an appropriate amount to elicit an immune response, e.g., the production of serum neutralizing antibodies, upon subsequent inoculation of the host.

The present invention is suitable for producing vaccines to a wide variety of viruses, including human viruses and animal viruses, such as canine, feline, bovine, porcine, equine, and ovine viruses. The method is suitable for inactivating double stranded DNA viruses, single-stranded DNA viruses, double-stranded RNA viruses, and single-stranded RNA viruses, including both enveloped and non-enveloped viruses. The following list is representative of those viruses which may be inactivated by the method of the present invention.

| Viruses which may be inactivated | |
|---|---|
| | Representative Viruses |
| dsDNA | |
| Adenoviruses | Adenovirus, canine adenovirus 2 |
| Herpesviruses | Herpes simplex viruses, Feline Herpes I |
| Papovaviruses | Polyoma, Papilloma |
| Poxviruses | Vaccinia |
| ssDNA | |
| Parvovirus | Canine parvovirus, Feline panleukopenia |
| dsRNA | |
| Orbiviruses | Bluetongue virus |
| Reoviruses | Reovirus |
| ssRNA | |
| Calicivirus | Feline calicivirus |
| Coronavirus | Feline infectious peritonitis |
| Myxovirus | Influenza virus |
| Paramyxovirus | Measles virus, Mumps virus, Newcastle disease virus, Canine distempter virus, Canine parainfluenza 2 virus |
| Picornavirus | Polio virus, Foot and mouth disease virus |
| Retrovirus | Feline leukemia virus, Human T-cell lymphoma virus, types I, II and III |
| Rhabdovirus | Vesicular stomatitis virus, rabies |
| Togavirus | Yellow fever virus, Sindbis virus, Encephalitis virus |

Of particular interest are those viruses for which conventional vaccine approaches have been unsuccessful or marginally successful. For such viruses, inactivation procedures which are sufficiently rigorous to assure the total loss of infectivity often result in partial or complete destruction of the antigenic characteristics of the virus. With such loss of antigenic characteristics, the viruses are incapable of eliciting a protective immunity when administered to a susceptible host. While it would be possible to utilize less rigorous inactivation conditions in order to preserve the antigenic integrity of the virus, this approach is not desirable since it can result in incomplete inactivation of the virus.

In preparing the subject vaccines, sufficient amounts of the virus to be inactivated may be obtained by growing seed virus in a suitable mammalian cell culture. Seed virus, in turn, may be obtained by isolation from an infected host. Suitable mammalian cell cultures include primary or secondary cultures derived from mammalian tissues or established cell lines such as Vero cells, monkey kidney cells, BHK21 hamster cells, LMTK$^-$ cells, and other cells permissive for the desired virus and which may be grown in vitro as monolayer or suspension cultures. The cell cultures are grown to approximately 80% saturation density, and infected with the virus at a low multiplicity of infection (MOI), usually between about 0.05 and 0.005, preferably at about 0.01.

After adsorbing the viral inoculum to the cells by incubation for a limited period of time at a temperature in the range from 35° C. to 40° C., an appropriate growth or maintenance medium is added. The cells are further incubated at about the same temperature, in the presence of about 5% carbon dioxide in air, until a sufficient amount of virus has been produced.

The growth and maintenance medium will usually be a conventional mammalian cell culture medium, such as Eagle's Minimum Essential Medium or Medium 199, usually supplemented with additives such as broth prepared from dehydrated standard microbial culture media, fetal bovine serum, fetal calf serum, or the like.

The furocoumarins useful for inactivation are primarily illustrated by the class of compounds referred to as psoralens, including psoralen and substituted psoralens where the substituents may be alkyl, particularly having from one to three carbon atoms, e.g., methyl; alkoxy, particularly having from one to three carbon atoms, e.g., methoxy; and substituted alkyl having from one to six, more usually from one to three carbon atoms and from one to two heteroatoms, which may be oxy, particularly hydroxy or alkoxy having from one to three carbon atoms, e.g., hydroxy methyl and methoxy methyl, or amino, including mono- and dialkyl amino or aminoalkyl, having a total of from zero to six carbon atoms, e.g., aminomethyl. There will be from 1 to 5, usually from 2 to 4 substituents, which will normally be at the 4, 5, 8, 4' and 5' positions, particularly at the 4' position. Illustrative compounds include 5-methoxypsoralen; 8-methoxypsoralen (8-MOP); 4,5',8-trimethylpsoralen (TMP); 4'-hydroxymethyl-4,5',8-trimethylpsoralen (HMT); 4'-aminomethyl-4,5',8-trimethylpsoralen (AMT); 4-methylpsoralen; 4,4'-dimethylpsoralen; 4,5'-dimethylpsoralen; 4',8-dimethylpsoralen; and 4'-methoxymethyl-4,5',8-trimethylpsoralen. Of particular interest are AMT and 8-MOP.

The furocoumarins may be used individually or in combination. Each of the furocoumarins may be present in amounts ranging from about 0.01 $\mu$g/ml to 1 mg/ml, preferably from about 0.5 $\mu$g/ml to 100 $\mu$g/ml, there not being less than about 1 $\mu$g/ml nor more than about 1 mg/ml or furocoumarins.

In carrying out the invention the furocoumarin(s), in an appropriate solvent which is substantially inert and sufficiently non-polar to allow for dissolution of the furocoumarin(s), are combined with the viral suspension, conveniently a viral suspension in an aqueous buffered medium, such as used for storage. The amount of virus will generally be about $1 \times 10^6$ to $10^{11}$, more usually about $1 \times 10^7$ to $10^9$ and preferably about $1 \times 10^8$ to $5 \times 10^8$ pfu/ml. The furocoumarin(s) will be at a concentration of about 0.001 mg/ml to 0.5 mg/ml, more usually about 0.05 mg/ml to 0.2 mg/ml. The amount of solvent which is usually to dissolve the furocoumarin will be sufficiently small so as to readily dissolve in the aqueous viral suspension.

Although viral inactivation according to the present invention will normally be carried out in an inactivation medium as just described, in some cases it may be desirable to introduce furocoumarins to the virus by addition to a cell culture medium in which the virus is grown. The inactivation is then carried out by separating the live viral particles from the culture medium, and exposure of the particles to ultraviolet light in an inactivation medium which may or may not contain additional furocoumarins. This method of inactivation is useful where the virus is resistant to inactivation when the furocoumarin is added to the inactivation medium only.

When employing furocoumarins with limited aqueous solubility, typically below about 50 μg/ml, it has been found useful to add an organic solvent, such as dimethyl sulfoxide (DMSO) ethanol, glycerol, polyethylene glycol (PEG) or polypropylene glycol, to the aqueous treatment solution. Such furocoumarins having limited solubility include 8-MOP, TMP, and psoralen. By adding small amounts of such organic solvents to the aqueous composition, typically in the range from about 1 to 25% by weight, more typically from about 2 to 10% by weight, the solubility of the furocoumarin can be increased to about 200 μg/ml, or higher. Such increased furocoumarin concentration may permit the use of shorter irradiation times. Also, inactivation of particularly recalcitrant microorganisms may be facilitated without having to increase the length or intensity of ultraviolet exposure, and the addition of an organic solvent may be necessary for inactivation of some viruses with particular furocoumarins. The ability to employ less rigorous inactivation conditions is of great benefit in preserving the antigenicity of the virus during inactivation.

At times, it may be desirable to employ organic solvents, particularly DMSO, with all furocoumarins regardless of solubility. For some microorganisms, particularly viruses having tight capsids, the addition of the organic solvent may increase the permeability of the outer coat or membrane of the microorganism. Such increase in permeability would facilitate penetration by the furocoumarins and enhances the inactivation of the microorganism.

The furocoumarin may be added to the viral suspension in a single addition or in multiple additions, where the virus is irradiated between additions, or may be added continuously during the entire treatment period, or a portion thereof. Usually, the number of additions will be from about 1 to 50, more usually from about 10 to 40, and preferably from about 2 to 4. The total amount of furocoumarin which will be added will be sufficient to provide a concentration of at least about 0.01 mg/ml to about 1 mg/ml, usually not more than about 0.75 mg/ml and preferably not more than about 0.5 mg/ml. Since a substantial proportion of the furocoumarin will have reacted with the nucleic acid between additions, the total concentration of furocoumarin in solution will generally not exceed about 0.1 mg/ml. In cases where the furocoumarin(s) employed are particularly unstable, it may be beneficial to add the furocoumarin solution continuously during the irradiation procedure.

In order to preserve the antigenic characteristics of the virus, irradiation is carried out in the substantial absence of oxygen and other oxidizing species. This is particularly important when employing psoralens that generate more singlet oxygen on a molar basis. For example, AMT generates more singlet oxygen than 8-MOP. Conveniently, oxygen and other gases may be removed from the inactivation medium by maintaining the medium in a non-oxidizing gas atmosphere, e.g., hydrogen, nitrogen, argon, helium, neon, carbon dioxide, and the like. The inactivation medium may be held in an enclosed vessel, and the space above the liquid medium surface filled with the non-oxidizing gas. Oxidizing species initially in the medium will be exchanged for the non-oxidizing gases according to gas-liquid equilibrium principles. Preferably, the space above the inactivation medium will be flushed with non-oxidizing gas to remove the oxidizing species and further lower their equilibrium concentration in the liquid medium. Depending on the volume of the inactivation medium, the flushing should be continued for at least 1 minute, preferably at least 2 minutes, usually being in the range from about 3 to 30 minutes. Flushing may be continued during the irradiation period, but need not be so long as the oxidizing species have been substantially removed and the vessel remains sealed to prevent the intrusion of air. Optionally, a singlet oxygen scavenger may be added to the inactivation medium prior to irradiation to further prevent interaction of oxygen with the furocoumarin and the virus. Suitable oxygen scavengers include ascorbic acid, dithioerythritol, sodium thionate, glutathione, and the like. The scavenger will be present at a concentration sufficient to block active oxygen species, usually being between 0.001M and 0.5M, more usually being between about 0.005M and 0.02M, where the addition may be in single, multiple, or continuous additions.

The concentration of dissolved oxygen may be reduced through the use of enzyme systems, either in solution or immobilized on a solid substrate. Suitable enzyme systems include glucose oxidase or catalase in the presence of glucose and ascorbic acid catalase in the presence of ascorbate. Such enzyme system may be employed alone or together with the other methods for oxygen reduction discussed above.

The total time for the irradiation will vary depending upon the light intensity, the concentration of the furocoumarin, the concentration of the virus, and the manner of irradiation of the virus, where the intensity of the irradiation may vary in the medium. The time of irradiation necessary for inactivation will be inversely proportional to the light intensity. The total time will usually be at least about 2 hrs. and not more than about 60 hrs., generally ranging from about 10 hrs. to 50 hrs. The times between additions of furocoumarin, where the furocoumarin is added incrementally, will generally vary from about 1 hour to 24 hrs., more usually from about 2 hrs. to 20 hrs.

The light which is employed will generally have a wavelength in the range from about 300 nm to 400 nm. Usually, an ultraviolet light source will be employed together with a filter for removing UVB light. The intensity will generally ranged form about 0.1 $mW/cm^2$ to about 5 $W/cm^2$, although in some cases, it may be much higher.

The temperature for the irradiation is preferably under 25° C., more preferably under 20° C. and will generally range from about −10° C. to 15° C., more usually from about 0° C. to 10° C.

During irradiation, the medium may be maintained still, stirred or circulated and may be either continuously irradiated or be subject to alternating periods of irradiation and non-irradiation. The circulation may be in a closed loop system or in a single pass system ensuring that all of the sample has been exposed to irradiation.

It may be desirable to remove the unexpended furocoumarin and/or its photobreakdown products from the irradiation mixture. This can be readily accomplished by one of several standard laboratory procedures such as dialysis across an appropriately sized membrane or through an appropriately sized hollow fiber system after completion of the irradiation. Alternatively, one could use affinity methods for one or more of the low molecular weight materials to be removed.

The inactivated virus may then be formulated in a variety of ways for use as a vaccine. The concentration of the virus will generally be from about $10^6$ to $10^9$ pfu/ml, as determined prior to inactivation, with a total dosage of at least $10^5$ pfu/dose, usually at least $10^6$ pfu/dose, preferably at least $10^7$ pfu/dose. The total dosage will usually be at or near about $10^9$ pfu/dose, more usually being about $10^8$ pfu/dose. The vaccine may include cells or may be cell-free. It may be an inert physiologically acceptable medium, such as ionized water, phosphate-buffered saline, saline, or the like, or may be administered in combination with a physiologically acceptable immunologic adjuvant, including but not limited to mineral oils, vegetable oils, mineral salts and immunopotentiators, such as muramyl dipeptide. The vaccine may be administered subcutaneously, intramuscularly, intraperitoneally, orally, or nasally. Usually, a specific dosage at a specific site will range from about 0.1 ml to 4 ml, where the total dosage will range from about 0.5 ml to 8 ml. The number of injections and their temporal spacing may be highly variable, but usually 1 to 3 injections at 1, 2 or 3 week intervals are effective.

The following examples are offered by way of illustration, not by way of limitation.

EXPERIMENTAL

Materials and Methods

A. Virus Growth and Tissue Culture

Hamster cells [BHK-21(C-13), American Type Culture Collection (ATCC), CCL 10] were grown as monolayers in plastic cell culture vessels in Eagle's Minimum Essential Medium (MEM) with Earle's salts and non-essential amino acids (MEN) supplemented with 10% heat inactivated calf serum ($C^i$) and 10% tryptose phosphate broth (Tp, e.g., Difco 0060). Cell cultures were used to produce live vesicular stomatitis virus, New Jersey serotype (VSV-NJ) from master seed virus originally obtained from the ATCC (VR-159), and live bluetongue virus (BTV) from master seed virus originally obtained from Dr. T. L. Barber, USDA, Denver, Colo. Cells were grown in culture vessels to 80% to 100% confluency (approximately $2 \times 10^5$ cells per $cm^2$ of growth surface area) using standard mammalian cell culture techniques. Corning plastic roller bottles (Corning No. 25140-850) with a growth surface area of 850 $cm^2$ containing 100 ml of MEN supplemented with 10% $C^i$ and 10% Tp and $1 \times 10^8$ to $2 \times 10^8$ CCL 10 cells/bottle were used for virus production. The cell cultures were initiated by seeding approximately $1 \times 10^6$ to $5 \times 10^7$ cells into 100 mls of growth medium in a roller bottle containing 5% $CO_2$ in air on a roller bottle rotator at 1 to 5 rpm at 35° C. to 38° C. The cultures were grown to 80% to 100% confluency over a six to fourteen day period with a medium change very two to four days.

When the monolayers reached 80% to 100% confluency, the culture medium was removed and the monolayer was infected with approximately $1 \times 10^6$ to $2 \times 10^6$ plaque forming units (pfu) of VSV or BTV in 20 mls of MEN, with 2% heat-inactivated fetal bovine serum ($F^i$) added for BTV. The multiplicity of infection (MOI) was approximately 0.01. The MOI may range from 0.001 pfu/cell to 0.033 pfu/cell. The virus inoculum was adsorbed to the cells by incubation at 35° C. to 38° C. for one hour at 1 to 5 rpm. One hundred mls of MEN containing 10% YELP supplement (v/v) for VSV, or 10% $C^i$ and 10% Tp for BTV, was added per roller bottle. YELP supplement contains: yeast extract BBL 11929, 5 g/liter; lactalbumin hydrolysate GIBCO 670-1800, 25 g/liter; and Bacto-Peptone (Difco 0118), 50 g/liter. The post-infection incubation was carried out at 35° C. to 38° C. in 5% $CO_2$/95% air with rotation. Sixteen to forty-eight hours post-infection, VSV cytopathic effect (CPE) was evident, while BTV CPE became apparent from 2 to 4 days post infection.

The CPE was characterized by cell rounding, cell detachment, and cell degeneration. When visual or microscopic examination indicated that at least 50% of the cell monolayer exhibited CPE, the contents of the roller bottle were swirled to remove loosely attached materials from the roller bottle walls. The harvest material was decanted from the roller bottles into centrifuge bottles. The crude VSV harvest was clarified by centrifugation at 500 to 1000 x g for 20 minutes, at 4° C. The BTV harvest was centrifuged at 2,000xg for 60 minutes at 4° C.

The clarified VSV preparations were concentrated by ultrafiltration using a Pellicon cassette system (Millipore XX42ASY60) with a cassette having a nominal exclusion limit of $10^5$ daltons (Millipore PTHK 000C5). The Pellicon cassette system was sterilized by filling the assembled unit with 1N NaOH and incubating the unit 12 to 24 hours at room temperature. The NaOH solution was pumped out of the cassette system and the system was flushed with two to four liters of sterile $H_2O$. The assembly and operation of the Pellicon system were in accordance with the instructions furnished by the manufacturer. All steps in the concentration were performed aseptically. The clarified VSV was concentrated 15 to 40 fold, dimethylsulfoxide (Sigma D-5879) added to a final concentration of 7.5% v/v, and suitable aliquots of the virus stored frozen at $-80°$ C. to $-100°$ C.

For BTV, the pellet resulting from centrifugation was resuspended aseptically in 8 ml of 2 mM Tris-HCl, pH 8.8, for each original roller bottle. The suspension was mixed vigorously on a vortex mixer, and/or sonicated at 4° C. for 1 min., and centrifuged at 1,400 x g for 30 min. at 4° C. The virus-containing supernatant was collected and the pellet was extracted twice more with 8 ml/roller bottle aliquots of 2 mM Tris-HCl, 8.8. The virus-containing supernatants were pooled and clarified by centrifugation at 4,000 x g for 30 min. at 4° C. The clarified supernatant was stored at 4° C.

Feline herpes I virus (FVR, the infective agent of feline viral rhinotracheitis) was grown as follows.

Cat cell lines AKD (ATCC CCL150) or Fc3Tg (ATCC CCL176) were grown as monolayers in plastic cell culture vessels in a standard defined culture medium consisting of MEN; F12K; MEM; or alpha MEM. Medium was supplemented with 2% to 15% inactivated fetal calf serum ($F^i$) or 2% to 20% YELP. Cell cultures were used to produce live Feline Herpes I virus from master seed virus derived from Feline Herpes I virus (ATCC VR636). Cells were grown in culture vessels to 80% to 100% confluency (approximately $1 \times 10^5$ to $2 \times 10^5$ cells per $cm^2$ of growth surface area) using standard mammalian cell culture techniques as follows.

Corning plastic roller bottles containing 50 to 100 ml of MEN supplemented with 10% $F^i$ and $1 \times 10^8$ to $2 \times 10^8$ AKD or Fc3Tg cells/bottles were used for Feline Herpes I virus production. The cell cultures were initiated by seeding approximately $1 \times 10^6$ to $5 \times 10^6$ cells into 50 to 100 mls of growth medium in a roller bottle containing about 5% $CO_2$ in air and incubating the roller bottle on a roller bottle rotator at 1 to 5 rpm at 35° C. to 38° C. The cultures were grown to 80% to 100% confluency over a 7 to 14 day period with a 100% medium change very 3 to 5 days.

When the monolayers were 80% to 100% confluent, the culture medium was removed and the monolayer was washed with 20 to 50 mls of phosphate buffered saline (PBS) pH 7.2 to 7.4 (NaCl 8 g+KCl 0.2 g+$Na_2HPO_4$ 1.14 g+$KH_2PO_4$ 0.2 g). The PBS wash was discarded, and the roller bottle was infected by the addition of approximately $1 \times 10^7$ to $2 \times 10^7$ plaque forming units (pfu) of Feline Herpes I virus in 10 mls of PBS containing 2% $F^i$. The multiplicity of infection (MOI) was approximately 0.1. The virus inoculum was adsorbed to the cells by incubation at 35° C. to 38° C. for one hour at 1 to 5 rpm. The inoculation fluid was removed and 50 mls of MEN containing 10% $F^i$ was added per roller bottle. The post-infection incubation was at 35° C. to 38° C. in 5% $CO_2$ in air with rotation. Herpesvirus cytopathic effect (CPE) was evident forty to forty-eight hours post-infection. The CPE was characterized by cell rounding, cell detachment, and cell degeneration.

The contents of the roller bottle were swirled 48 hours post-infection to remove loosely attached materials from the roller bottle walls, and the contents of the roller bottles were decanted into centrifuge bottles. The virus, cells, and cell debris were pelleted by centrifugation at 10,000 x g for 30 minutes.

Cell associated (CA) Feline Herpes I virus was prepared by:

1. resuspending the 10,000 x g pellet in approximately 5 ml of a resuspension medium containing 80 parts F12K, 10 parts $F^i$, and 10 parts dimethylsulfoxide (DMSO) for each original roller bottle;
2. freezing the resuspended CA virus at −20° C. for 1.5 to 2 hours; and
3. transferring the CA virus frozen at −20° C. to temperatures ranging from −80° C. to −100° C.

Cell free (CF) Feline Herpes I virus was prepared by:

1. resuspending the 10,000 x g pellet in F12K;
2. freezing and thawing the resuspended material 3 times;
3. clarifying the freeze-thawed material by centrifugation at 10,000 x g for 30 minutes; and
4. freezing the clarified supernatant (CF virus) at temperatures ranging from −80° C. to −100° C.

CF or CA virus was thawed by gentle agitation at 37° C. in a water bath.

B. Virus Assay

Confluent monolayers of LMTK−, Vero (ATCC CCL 81), Fc3Tg, or AKD cells were prepared in 6 cm diameter mammalian cell culture plastic petri dishes (Corning #25010) or other convenient cell culture vessels. The growth medium used for LMTK− cells was alpha ME (alpha modified Eagles Minimum Essential Medium, Earle's Salts)+10% $F^i$. The growth medium used for Vero cells was MEN+5% $F^i$. The growth medium used for Fc3Tg cells was MEN+10% $F^i$, and the growth medium used for AKD cells was F12K+15% $F^i$ (VSV and BTV were titered on LMTK− or Vero cells. Feline Herpes I was titered on Fc3Tg or AKD cells). Ten fold serial dilutions of virus samples were made by adding 0.5 ml of the virus sample to 4.5 mls of diluent (phosphate buffered saline, pH 7.2 to 7.4, plus 2% $F^i$) in a screw cap tube. The growth medium was removed from a 6 cm culture dish cell monolayer, 0.1 ml of virus sample (undiluted or diluted) was added, and the virus was adsorbed to the monolayer for 1 to 2 hours at 35° C. to 38° C. Two or more monolayers were used for each sample.

Five ml of overlay medium was added per 6 cm culture dish, except for Feline Herpes I, where the unadsorbed inoculum was removed, and 4 mls of overlay medium was added per 6 cm culture dish. The overlay medium for BTV or VSV was prepared by mixing equal parts of solution A (100 ml 2X MEM with L-glutamine, GIBCO #320-1935, +10 ml $F^i$) and 1.8% to 2% Noble Agar (Difco 0142) in deionized $H_2O$ at 44° C. to 45° C. The overlay medium for Feline Herpes I was prepared by mixing equal parts solution A and 1% methyl cellulose (4,000 centriposes) in deionized $H_2O$ (Fisher M-281 sterilized by autoclaving).

The virus infected cultures were incubated at 35° C. to 38° C. in 5% $CO_2$ in air. Twenty-four hours before plaques were counted, a second overlay containing Neutral Red at a final concentration of 0.005% was added. Plaques were counted on day 2 or day 3 post-infection for VSV, on day 2 to 4 for FVR and on day 6 or 7 for BTV. The virus titer in pfu/ml was calculated by multiplying the average number of plaques per dish by the reciprocal of the dilution. The pfu/ml was the value used to determine the amount of virus needed to infect cells at a MOI of approximately 0.01. The pfu/ml in a virus preparation prior to inactivation was used to determine the immunizing dose.

C. Virus Inactivation

1. VSV Inactivation

The thawed stock of VSV was pipetted into sterile T-150 tissue culture flasks (nominally 25 ml into each of four flasks). To each flask was added 0.25 ml of 4′-aminomethyl-4,5′,8-trimethylpsoralen (AMT) stock solution (stock solution is 1 mg/ml AMT dissolved in sterile, deionized water). Each flask was allowed to equilibrate in an argon atmosphere for at least 10 minutes. After equilibration, a stream of argon gas was directed into each flask for at least two minutes. The flasks were then tightly capped and placed under a long wavelength ultraviolet (320 nm to 400 nm) light source (GE BLB fluorescent bulbs) at a temperature between 0° C. and 20° C. for approximately 11 hours. The incident light intensity was approximately 1 mW/cm² (measured by a J-221 long wavelength UV meter).

After the irradiation was completed, the flasks were removed from the light source and an additional 0.25 ml of AMT stock solution was mixed into each flask. The contents of each flask were pipetted into new, sterile T-150 flasks, and the flasks were again flushed with argon and irradiated for an additional 11 hours. This procedure was repeated three more times until five additions (a total of approx. 50 μg/ml) of AMT had been performed, the virus sample had been irradiated for at least 55 hours, and at least four flask changed has been performed.

After all of the irradiations had been completed, the contents of the flasks were aseptically transferred to a common sterile container and stored at −85° C.

2. BTV Inactivation

Twenty-five ml of BTV serotype 11 ($1.5 \times 10^8$ pfu/ml) was mixed with 0.25 ml of 4′-aminomethyl 4,5′,8-trimethylpsoralen (AMT; 1 mg/ml in DMSO).

The mixture was placed in a 150 cm² tissue culture flask (T-150; Corning #251201). The viral suspension in the flask was placed in an argon atmosphere for 10 min., and a stream of argon gas was then blown over the viral suspension for an additional 2 min. The flask was tightly capped and the suspension irradiated for 3.25 hrs. at 4° C. using GE BLB fluorescent bulbs at an intensity of 1.5 mW/cm². An additional 0.25 ml of AMT was then added to the viral suspension, the suspension transferred by pipette to a new T-150 flask, and the solution again flushed with argon. The flask was irradiated for an additional 14.75 hours at 4° C. under the same long wavelength UV light source. After this irradiation an additional 0.25 ml of AMT solution was added to the suspension, and it was again transferred to a new T-150 flask. The solution was flushed with argon as before and irradiated for an additional 5.5 hrs. at 4° C. The inactivated BTV was stored at 4° C.

3. Feline Herpes I Inactivation a. Cell Free Virus

Nineteen mls of CF-FVR ($1.9\times10^7$ pfu/ml) were mixed with 0.4 ml of hydroxymethyltrioxsalen (HMT; 1 mg/ml in DMSO) and 1.9 ml of sodium ascorbate (0.1M in $H_2O$). The mixture was prepared in 150 $cm^2$ tissue culture flasks (T-150, Corning No. 25120) that were subsequently deaerated for 2 minutes with pure argon gas. The virus-containing flasks were irradiated for 55 minutes at 4° C. using G.E. BLB fluorescent bulbs at an intensity of 1.5 $mW/cm^2$. The FVR/HMT/ascorbate mixture was then transferred by pipet into a second T-150 flask, which was deaerated for 2 minutes using pure argon gas. The second T-150 flask was irradiated for an additional 28 minutes at 4° C. under the same long wavelength UV light source.

The CF-FVR preparation was stored at −100° C. in a REVCO freezer. Subsequently the CF-FVR preparation was thawed and placed into a T-150 flask. The flask was deaerated with pure argon gas for 2 minutes and irradiation was continued as described above for an additional 15 hours and 40 minutes.

b. Cell Associated Virus

Cells from 10 roller bottles (about $1\times10^8$ to $2\times10^8$ cells/roller bottle) were resuspended in 28 mls of cell culture media. Twenty mls of the suspension were placed into a T-150 flask. To this flask was added 2 ml of freshly prepared sterile 0.1M sodium ascorbate and 0.4 ml HMT (1 mg/ml in DMSO). The flask was deaerated with pure argon gas for 2 minutes, and the flask was irradiated at 4° C. using G.E. BLB fluorescent bulbs at an intensity of 1.5 $mW/cm^2$ for 75 minutes. The viral suspension was then transferred by pipet from the T-150 flask into a second T-150 flask and again deaerated with pure argon gas for 2 minutes. Irradiation was continued for an additional 95 minutes. The CA-FVR preparation was adjusted to 10% DMSO and the suspension was frozen at −20° C. for 1 hour and then stored at −100° C. in a REVCO freezer.

The stored frozen CA-FVR preparation was subsequently thawed, and the cells were pelleted in a clinical centrifuge. The cells were resuspended in 21 mls of serum-free medium to which 2.1 mls of freshly prepared 0.1M sodium ascorbate and 0.4 ml of HMT (1 mg/ml in DMSO) were added. The sample was transferred by pipet to a T-150 flask, and irradiation was continued for an additional 15 hours and 40 minutes.

Results

A. Bluetongue Virus

1. Assessment of Inactivation by Blind Passage

CCL 10 cells were grown to confluency in 850 $cm^2$ roller bottles using standard cell culture procedures, as described above. The culture medium was removed from the roller bottle, and 2.0 ml of the inactivated virus preparation mixed with 18 ml of medium containing 2% $F^i$ was adsorbed to the roller bottle cell monolayer for 60 min at 35° C. to 38° C. with rotation at 1 to 5 rpm. After adsorption, the residual unabsorbed inoculum was removed, and 100 ml of growth medium (MEN with 10% $C^i$ and 10% Tp) was added and the roller bottle culture incubated at 35° C. to 38° C. for 7 days with daily observation for viral CPE. The roller bottle culture received a 100% medium change every 2 to 3 days. If no CPE was observed during the first roller bottle passage, the cell monolayer was chilled at 4° C. for 12 to 24 hrs. The cells were scraped into the medium which was then decanted into a centrifuge bottle. The cells were pelleted by centrifugation at 4° C. at 2,000 x g for 30 min. and resuspended in 2.0 ml of 2 mM Tris-HCl (pH 8.8) by vigorous mixing using a vortex mixer. The resuspended material was centrifuged at 2,000 x g for 20 min. at 4° C. The supernatant was added to 18 ml of growth medium containing 2% $F^i$ and used to infect a new confluent roller bottle culture of CCL 10 cells, as described immediately above. The second roller bottle blind passage was observed for 7 days and fed every 2 to 3 days. If no CPE was observed during the second roller bottle blind passage, a third roller bottle blind passage was performed. If no CPE had been observed by the end of the third roller bottle blind passage the virus preparation was considered inactivated and suitable for in vivo testing.

2. Immunization of Rabbits with Psoralen-inactivated BTV Vaccine a. Example 1

Four New Zealand white rabbits were randomly assigned to 2 groups, designated A and B. Both groups were given 4 immunizations at two week intervals. The first immunization consisted of 1 ml of vaccine ($10^8$ pfu BTV serotype 11) and 1 ml of Freund's Complete Adjuvant. The second through fourth immunizations utilized 1 ml of vaccine ($10^8$ pfu BTV serotype 11) and 1 ml of Freund's Incomplete Adjuvant. All immunizations were given intramuscularly (IM). The vaccine given to Group A (Vaccine #1) was inactivated with AMT-UVA in the presence of 0.01M ascorbic acid. Vaccine #1 was dialyzed for 12 hours against 2 mM Tris, pH 8.6. The vaccine given to Group B (Vaccine #2) was inactivated with AMT-UVA without ascorbic acid and sonicated three times (2 minutes each time) using a cup horn probe (Heat Systems Model 431A) at a power setting of 3 (Heat Systems Model W220). Both Vaccine #1 and Vaccine #2 were deemed inactivated since no live virus was detected during blind passage. Inactivated vaccine was also tested for safety by chicken embryo inoculation. Egg deaths attributable to live virus were not encountered. Both rabbit groups were bled via auricular venipuncture one week following the second, third, and fourth immunizations. Serum from each rabbit was pooled with that of its groupmate, and the pooled sera were tested for anti-BTV antibodies by two standard serologic assays, serum neutralization (Jochim and Jones, *Am. J. Vet. Res.* (1976) 37:1345–1347) and agar gel precipitation (Jochim et al., Am. Assoc. Vet. Lab. Diag., 22nd Proceed.: 463–471, 1979). Pre-immunization rabbit serum was used as the negative control; BTV immune sheep serum was used as the positive control for both immunologic procedures.

Pooled sera from Groups A and B reduced the number of viral plaques (serum neutralization) greater than eighty percent (arbitrarily selected end point) when the sera were diluted 1:40, which was the highest dilution examined. Negative and positive control sera behaved as expected.

TABLE 1

Serum Neutralization Data From Rabbits Vaccinated with AMT-UVA-inactivated Bluetongue Virus Vaccines.

| Group | Titer*: 1 | 5 | 40 |
|---|---|---|---|
| A | + | + | + |
| B | + | + | + |
| Normal Rabbit Serum | − | − | − |
| BTV-Immune Sheep Serum | + | + | ± |

*Reciprocal of serum dilution neutralizing 80 percent of BTV plaque activity on BHK cells. The data are from the post-second immunization serum samples.

Pooled post-immunization sera from Groups A and B precipitated BTV antigen in immunodiffusion plates when tested at dilutions up to 1:16. Normal rabbit serum did not precipitate the standard BTV antigen. BTV-immune sheep serum did precipitate the BTV antigen, but not at dilutions greater than 1:2.

Of the two immunologic procedures utilized, serum neutralization is considered predictive for immunity to live BTV challenge in the target species.

b. Example 2

Twelve New Zealand white rabbits were randomly assigned to six groups, A–F, two rabbits per group. An additional four rabbits were assigned to Group G. These sixteen rabbits were vaccinated twice subcutaneously with the AMT-UVA inactivated Bluetongue virus vaccines described in Table 2. Preinactivation titer was approximately $10^8$ for each serotype. The vaccines were formulated with 20% (v/v) aluminum hydroxide adjuvant, and were given with a three week interval between the first and second inoculations.

The sixteen rabbits were bled by auricular venipuncture on days 0, 14 and 35. Each serum was heat-inactivated and tested against BTV serotypes 10, 11, 13 and 17 for serum neutralizing antibody. All vaccinated rabbits developed SN titers against the homologous vaccine serotypes (Table 3). These data demonstrated the immunopotency of a multivalent AMT-UVA inactivated Bluetongue virus vaccine.

TABLE 2

Serotype Composition of Inactivated Bluetongue Virus Vaccines Tested in Rabbits

| Group | Rabbit # | BTV Serotype Composition |
|---|---|---|
| A | 1, 2 | 10 |
| B | 3, 4 | 11 |
| C | 5, 6 | 13 |
| D | 7, 8 | 17 |
| E | 9, 10 | 11, 17 |
| F | 11, 12 | 10, 11, 17 |
| G | 13, 14, 15, 16 | 10, 11, 13, 17 |

TABLE 3

Serum Neutralizing Data from Rabbits Vaccinated with AMT-UVA Single and Multi-Serotype Bluetongue Virus Vaccines

| Group | Rabbit | SN Titer* Against: BTV-10 | BTV-11 | BTV-13 | BTV-17 |
|---|---|---|---|---|---|
| A | 1 | 1:160 | 1:10 | 1:10 | 1:10 |
| | 2 | 1:320 | 1:10 | 1:10 | 1:10 |
| | 3 | 1:10 | 1:320 | 1:10 | 1:10 |
| B | 4 | 1:10 | 1:80 | 1:10 | 1:10 |
| | 5 | 1:20 | 1:20 | 1:160 | 1:10 |
| C | 6 | 1:20 | 1:10 | 1:40 | 1:10 |
| | 7 | 1:10 | 1:10 | 1:10 | 1:320 |
| D | 8 | 1:10 | 1:10 | 1:10 | 1:320 |
| | 9 | 1:20 | 1:160 | 1:20 | 1:160 |
| E | 10 | 1:20 | 1:160 | 1:20 | 1:160 |
| | 11 | 1:160 | 1:160 | 1:20 | 1:160 |
| F | 12 | 1:40 | 1:40 | 1:20 | 1:80 |
| | 13 | 1:160 | 1:160 | 1:80 | 1:160 |
| | 14 | 1:160 | 1:160 | 1:80 | 1:160 |
| G | 15 | 1:160 | 1:160 | 1:40 | 1:160 |
| | 16 | 1:80 | 1:160 | 1:160 | 1:160 |

*Reciprocal of serum dilution neutralizing 80% of BTV plaque activity on Vero cells. The data are from the post-second immunization sera (Day 35). Negative and positive control sera behaved as expected in the SN assay.

3. Immunization of Sheep with Psoralen-inactivated BTV Vaccine a. Example 1

Each of two adult sheep, known to be susceptible to BTV, was inoculated subcutaneously (SQ) with 2 ml of AMT-UVA inactivated BTV plus adjuvant (1:1, vaccine to aluminum hydroxide adjuvant). The vaccine contained approximately $10^8$ pfu/ml of BTV prior to inactivation. A third sheep was inoculated SQ with 6 ml of the identical vaccine without adjuvant. Seven weeks later the three sheep were given identical inoculations SQ that consisted of 5 ml of vaccine and aluminum hydroxide adjuvant (2:1 vaccine to adjuvant; $10^8$ pfu BTV/ml of vaccine).

The three sheep were monitored for clinical evidence of BTV, including daily body temperature recording and bi-daily virus isolation attempts. No evidence of BTV was observed, indicating that the vaccine was inactivated.

Serum was collected weekly for serum neutralization and agar gel precipitation testing. Normal sheep sera and BTV-immune sheep sera were used for negative and positive control samples in the serologic tests.

The first vaccine inoculations induced precipitating anti-BTV antibody in all three sheep. Their pre-exposure sera were uniformly negative for anti-BTV precipitating antibody. Modest neutralizing anti-BTV antibody titers (1:5) were elicited in two of three sheep following one immunization. The second immunization elicited a distinct immunological anamnestic response, inducing neutralizing titers of 1:40, 1:80, or 1:160 in the three sheep.

TABLE 4

Serum Neutralization Data From Sheep Immunized with an AMT-UVA Inactivated BTV Vaccine.

| | TITERS* Sheep No.: | | |
|---|---|---|---|
| | 1 | 2 | 3 |
| Pre-First Immunization | | | |
| Day 0 | <5 | <5 | <5 |
| Post-First Immunization | | | |
| Day 21 | 5 | 5 | <5 |
| Post-Second Immunization | | | |
| Day 7 | 80 | 160 | 40 |
| Day 14 | 80 | 40 | 40 |

TABLE 4-continued

Serum Neutralization Data From Sheep Immunized with an AMT-UVA Inactivated BTV Vaccine.

| | TITERS* Sheep No.: | | |
|---|---|---|---|
| | 1 | 2 | 3 |
| Day 21 | 80 | 80 | 40 |
| Day 42 | 80 | 80 | 80 |
| Post-Challenge | | | |
| Day 7 | 160 | 160 | 80 |
| Day 14 | 320 | 160 | 80 |

*Reciprocal of highest 2-fold dilution reducing BTV plaque activity on BHK cells by 80 percent.

The sheep were challenged by SQ syringe inoculation of $10^5$ egg lethal doses of BTV serotype 11. The three sheep remained clinically normal during the BTV challenge period, indicating that the vaccine was efficaceous.

It is evident from the above results that the BTV which is psoralen-inactivated retains its immunogenicity, particularly as to those sites which elicit an immune response which is effective in protecting a host against subsequent BTV-infection. Thus, the psoralen inactivation can be carried out under conditions which do not modify the immunogenic sites of the virus, so as to elicit an immunogenic response which will be effective against the live BTV. Furthermore, the BTV RNA virus is efficiently inactivated under mild conditions to the point of complete inactivation, whence it may be safely administered to a host.

b. Example 2

Eight experimental and four control sheep, known to be Bluetongue Virus susceptible, were housed together in an insect-proof facility. The experimental sheep were inoculated twice subcutaneously with AMT-UVA inactivated BTV Serotype 11 vaccine. Each vaccinate received approximately $3 \times 10^8$ pfu BTV-11 formulated with twenty-five percent (v/v) aluminum hydroxide adjuvant. Three weeks elapsed between immunizations. Control sheep were inoculated with tissue culture fluid in 25% percent (v/v) aluminum hydroxide. Serum samples were collected prior to vaccination, following vaccinations, and following challenge, and tested for SN antibodies. All sheep were challenged by subcutaneous inoculation of $2 \times 10^5$ $ELD_{50}$ BTV-11 four weeks post-second vaccination. Virus isolation was performed twice weekly post-challenge for six weeks. Virus isolation from sheep blood was done by intravenous chicken embryo inoculation, followed by specific BTV serotype identification by neutralization in vitro.

Five of the eight vaccinated sheep developed SN titers of 1:20 post-second vaccination. All eight vaccinates resisted subcutaneous challenge with $2 \times 10^5$ $ELD_{50}$ BTV-11, whereas the four control sheep developed uniform viremia as assessed by egg inoculation. Sheep data are given in Table 5.

TABLE 5

Serum Neutralization and Virus Isolution Data from Sheep Vaccinated with AMT-UVA Inactivated BTV-11 Vaccine and Subsequently Challenged with $2 \times 10^5$ $ELD_{50}$ of Live BTV-11

| Sheep No. | Baseline | SN Titer Post-Second Vaccination | Post-Challenge | Virus Isolation Post-Challenge Day | | | |
|---|---|---|---|---|---|---|---|
| | | | | 4 | 11 | 15 | 18 |
| Experimental | | | | | | | |
| 650 | neg | 1:20 | 1:160 | — | — | — | — |
| 651 | neg | 1:20 | 1:40 | — | — | — | — |
| 652 | neg | 1:20 | 1:160 | — | — | — | — |
| 653 | neg | 1:20 | 1:40 | — | — | — | — |
| 656 | neg | 1:10 | 1:160 | — | — | — | — |
| 658 | neg | 1:10 | 1:40 | — | — | — | — |
| 659 | neg | 1:20 | 1:160 | — | — | — | — |
| 660 | neg | 1:10 | 1:160 | — | — | — | — |
| Controls | | | | | | | |
| 654 | neg | neg | 1:10 | + | + | + | + |
| 655 | neg | neg | neg | + | + | + | + |
| 661 | neg | neg | 1:40 | + | + | + | + |
| 662 | neg | neg | 1:160 | + | + | + | — |

B. Feline Herpes Virus I

1. Assessment of Inactivation by Blind Passage

Fc3Tg or AKD cells were grown to confluency in 850 $cm^2$ roller bottles using standard cell culture procedures as described above. The culture medium was removed from the roller bottle, and 2.0 mls of the inactivated virus preparation, mixed with 18 mls of medium containing 2% $F^i$, were adsorbed to the roller bottle cell monolayer for 60 minutes at 35° C. to 38° C. with rotation at 1 to 5 rpm. After adsorption, the inoculum was removed and 150 ml of maintenance medium (MEN or F12K with 2% $F^i$) added. The roller bottle culture was then incubated at 35° C. to 38° C. for 7 days with daily observation for viral CPE. The roller bottle culture received a 100% medium change after 3 to 5 days. If no CPE was observed during the first roller bottle passage, the cell monolayer was scraped into the maintenance medium which was then decanted into a centrifuge bottle. The cells were pelleted by centrifugation at room temperature at 1,000 x g for 15 minutes, resuspended in 20 ml of fresh maintenance medium, and passed to a new confluent roller bottle culture of Fc3Tg or AKD cells as described above. The second roller bottle blind passage was observed for 7 days and fed once on day 3 to 5. If no CPE was observed during the second roller bottle blind passage, a third roller bottle blind passage was performed. If no CPE was observed by the end of the third roller bottle passage, the virus preparation was considered inactive.

2. Administration Procedure for Psoralen-inactivated FVR Vaccines

Photochemically inactivated FVR was inoculated via syringe into cats by various routes, including but not limited to intravenously (IV), subcutaneously (SQ), intramuscularly (IM), or intraperitoneally (IP). The vaccine was administered in various volumes (0.5 to 3.0 ml) and in various concentrations ($10^6$ to $10^8$ pfu; either CF, CA or in combination). In the following examples, the vaccine was administered in combination with aluminum hydroxide as an immunologic adjuvant. The number of injections and their temporal spacing was as set forth in each example.

3. Immunization with Psoralen-inactivated CR-FVR Vaccine

The experimental group consisted of four specific pathogen free kittens (2 males, 2 females) four months old (Liberty Laboratories, Liberty Corner, N.J.). The control group consisting of two similar female kittens. The experimental group was inoculated IM with $3\times10^7$ pfu (3 mls) of HMT inactivated CF-FVR on days 0 and 21, and again inoculated with $3\times10^7$ pfu HMT inactivated with an equal amount of 2% aluminum hydroxide [Al(OH)$_3$] adjuvant on day 61. Controls were vaccinated at eight weeks and at thirteen weeks of age with a commercial FVR vaccine using the manufacturer's recommended procedure. Serum samples were collected weekly and tested for anti-FVR neutralizing antibodies.

Following live virus challenge ($10^6$ pfu intranasally and intraconjunctivally), a numerical scoring system (Table 6) was used to assess the clinical response of both experimental and control cats.

TABLE 6

Scoring System for Clinical Effects of Herpesvirus Challenge in Cats

| Factor | Degree | Score |
|---|---|---|
| Fever | 101 to 102° F. | 0 |
|  | 102 to 103 | 1 |
|  | 103 to 104 | 3 |
|  | greater than 104 | 5 |
| Depression | slight | 1 |
|  | moderate | 3 |
|  | severe | 5 |
| Sneezing | occasional | 1 |
|  | moderate | 3 |
|  | paroxysmal | 5 |
| Lacrimation | serous | 1 |
|  | mucoid | 3 |
|  | purulent | 5 |
| Nasal Discharge | serous | 1 |
|  | mucoid | 3 |
|  | purulent | 5 |
| Appetite | normal; eats all food | 0 |
|  | fair; eats more than ½ of food | 1 |
|  | poor; eats less than ½ of food | 3 |
|  | none; eats nothing | 5 |

Three of four experimental cats developed serum neutralizing anti-FVR antibody (SN) titers of 1:2 that were detected between day 42 and day 58. Following the third immunization (day 61), four of four experimental cats had SN titers of 1:4 (day 80). Baseline SN antibody titers on the experimental cats were negative. The control cats did not develop detectable SN antibody titers during the pre-challenge period.

All cats were exposed to $10^6$ pfu of live FVR by intraconjunctival and intransal exposure on day 91. Each cat was monitored twice daily for the absence, presence and degree of severity of factors given in Table 6. A composite clinical score was derived for each cat after a 15 day observation period.

Three of four experimental cats demonstrated mild temperature elevation and serous ocular or nasal discharge along with mild intermittent depression and appetite suppression. Their composite scores were 39, 42, and 35 respectively for the 15 day observation period. The fourth experimental cat was more severly affected (composite score=84) by moderate, but transient, sneezing and mucoid nasal discharge. Both control cats were severely affected by live virus challenge. Severe purulent nasal and ocular discharge and lack of appetite were apparent. The control cats had composite scores of 133 and 253.

Three weeks following live FVR challenge, all cats were tested for SN antibody titers against FVR. Three of four experimental cats had SN antibody titers of 1:16 while the fourth cat had a 1:8 titer. One of the control cats has an SN antibody titer of 1:4 while the second control lacked an SN antibody titer against FVR.

4. Immunization with Psoralen-inactivated CA-FVR Vaccine

Nine age-matched specific pathogen free kittens, 4 months old (Liberty Laboratories, Liberty Corner, N.J.), were randomly assigned to three experimental groups designated A, B, and C.

Group A (controls) was inoculated twice with 1 ml tissue culture fluid and 1 ml aluminum hydroxide adjuvant. Group B was inoculated twice with a commercial FVR vaccine according to the manufacturer's recommendation. Group C was inoculated three times with $10^7$ HMT-inactivated CA-FVR in aluminum hydroxide (total volume=2 ml; 1:1 vaccine to adjuvant). All injections were given IM at three week intervals.

Live FVR virus ($10^6$ pfu intranasally and intraconjunctivally) was given on day 63 and a numerical scoring system (Table 6) was used to assess the kittens' clinical response for a 15 day post-challenge period. Serum samples were collected from all kittens prior to vaccination, prior to the second and third immunizations, prior to live FVR challenge, and at 15 days post-challenge. The sera were utilized to assess neutralizing antibody titers by standard procedures.

The control kittens (Group A) maintained SN antibody titers less than 1:2 (negative) throughout the pre-challenged period. Fifteen days following live FVR challenge Group A kittens uniformly had SN antibody titers of 1:2. Kittens in Groups B and C lacked detectable anti-FVR antibody titers pre-immunization, but all kittens in Groups B and C had SN antibody titers of 1:2 or 1:4 after two immunizations. The third immunization in Group C kittens did not significantly alter their SN antibody titers. Following a 15 day post-challenge period, kittens in Groups B and C demonstrated an anamnestic immunologic response, with SN antibody titers ranging from 1:16 to 1:64.

Clinically, Group A kittens were severely affected by live FVR challenge, whereas kittens in Groups B and C were significantly protected by their respective vaccines.

The composite clinical scores for Group A were 125, 141, and 128 for the 15 day post-challenge period. The composite clinical scores for Group B were 25, 20, and 64, while Group C had composite clinical scores of 21, 15, and 34. The clinical signs evident were characteristic of FVR.

From the SN data and clinical scoring, it is evident that kittens immunized with the experimental HMT-inactivated FVR vaccines (cell-free or cell associated) in the above examples were significantly immune to the clinical effects of severe FVR challenge.

C. Vesicular Stomatitis Virus

1. Assessment of Inactivation by Intracerebral Inoculation of Mice

Suckling mice (0 to 10 days old) were inoculated intracerebrally with 0.02 ml of the psoralen-inactivated VSV-NJ using a tuberculin syringe and a 28 or 30 gauge needle. Each vaccine lot was tested in four to nine suckling mice. The mice were observed three times daily for a minimum of seven days. Residual low-level live VSV kills suckling mice in two to five days. The sensitivity of this assay is approximately 1 to 5 pfu of live VSV per intracerebral dose. Inactivated VSV-NJ vaccine was considered safe (inactivated) if all inoculated suckling mice survived the seven day observation period. The VSV-NJ vaccine batches used hereinafter each passed the suckling mouse safety test prior to use.

2. Virus Neutralization in Mice Immunized with Psoralen-inactivated VSV-NJ Vaccine Groups of ten adult white mice each were injected using three immunological adjuvants (aluminum hydroxide gel, incomplete Freund's, or oil emulsion) with one of three psoralen-inactivated VSV-NJ vaccine doses ($10^9$, $10^8$, or $10^7$ pfu/dose). The oil emulsion was prepared as described by Stone et al. (1978) Avian Dis. 22:666-674. All mice were injected IP once each, on day 0 and day 21. Serum samples were collected from the orbital sinus on day 20 and on day 33 and pooled serum samples were assessed for serum neutralization (SN) activity by standard procedures. See, Castaneda et al. (1964) Proc. US Livestock San. Assoc. 68:455-468. Serum samples were negative for neutralizing antibodies to VSV-NJ prior to vaccination.

The vaccine with oil emulsion adjuvant induced the highest SN titers after one injection. All three vaccine doses, regardless of adjuvant, induced SN titers of at least 1:2000 after two injections. Serum dilutions were tested for SN activity only to 1:2560. The results are set forth in Table 7.

TABLE 7

Virus Neutralization Indices* of Mouse Sera After One and Two Injections of Psoralen-Inactivated VSV-NJ Vaccine

| Adjuvant | No. of Injections | $Log_{10}$ of Vaccine Concentration (pfu/dose) | | |
|---|---|---|---|---|
| | | 7 | 8 | 9 |
| Aluminum hydroxide gel | 1 | 67* | 905 | 905 |
| Aluminum hydroxide gel | 2 | >2560 | 2560 | >2560 |
| Freund's Incomplete | 1 | 226 | 57 | 905 |
| Freund's Incomplete | 2 | 2033 | >2560 | >2560 |
| Oil Emulsion | 1 | >2560 | >2560 | 2357 |
| Oil Emulsion | 2 | >2560 | >2560 | >2560 |

*Virus neutralization index is the reciprocal of the serum dilution that neutralized 32 $TCID_{50}$ of VSV-NJ.

3. Virus Neutralization in Hamsters Vaccinated with Psoralen-inactivated VSV-NJ Vaccine Groups of five MHA hamsters each were injected with either $10^9$, $10^8$, or $10^7$ pfu psoralen-inactivated VSV-NJ per dose, with or without aluminum hydroxide adjuvant (1:1). All hamsters were injected intramuscularly (IM) once each, on day 0 and again on day 21. Pooled serum samples were collected on day 21 and on day 34 for serum neutralization testing by standard procedures. Serum neutralizing antibodies were elicited by all three vaccine doses tested, with or without aluminum hydroxide adjuvant. SN titers are given in Table 8.

TABLE 8

Virus Neutralization Indices* of Hamster Sera After One and Two Injections of Psoralen-Inactivated VSV-NJ Vaccine

| Adjuvant | No. of Injections | $Log_{10}$ of Vaccine Concentration (pfu/dose) | | |
|---|---|---|---|---|
| | | 7 | 8 | 9 |
| None | 1 | 134* | 134 | 1076 |
| None | 2 | 1280 | 1810 | >2560 |
| Aluminum hydroxide gel | 1 | 538 | 538 | >2560 |
| Aluminum hydroxide gel | 2 | 1810 | 1920 | 2560 |

*Virus neutralization index is the reciprocal of the serum dilution that neutralized 32 $TCID_{50}$ of VSV-NJ.

4. Live VSV-NJ Challenge of Mice Vaccinated with Psoralen-inactivated VSV-NJ Vaccine Three groups of fourteen, sixteen and seventeen adult white mice each were injected with either $10^7$, $10^6$ or $10^5$ pfu psoralen-inactivated VSV-NJ per dose, respectively, using oil emulsion adjuvant with all injections. Each mouse was injected once IP (day 0). Pooled serum samples were collected on day 0 and again on day 21, and these samples were tested for SN antibody titers by standard procedures. The results are set forth in Table 9.

TABLE 9

Virus Neutralization Indices* of Mouse Sera After One Injection With Psoralen-Inactivated VSV-NJ Vaccine, Using Oil Emulsion Adjuvant

| Day | $Log_{10}$ of Vaccine Concentration (pfu/dose) | | |
|---|---|---|---|
| | 5 | 6 | 7 |
| 0 | —* | — | — |
| 21 | — | — | 40 |

*Virus neutralization index is the reciprocal of the serum dilution that neutralized 56 $TCID_{50}$ of VSV-NJ Each group of mice was subdivided into three groups of about five mice each. Each mouse was challenged with either 1, 10 or 100 minimum lethal doses (MLD) of live VSV by intracerebral inoculation on day 33.

Two of five mice that were immunized with $10^6$ pfu psoralen-inactivated VSV-NJ survived a one MLD VSV challenge but five of five mice that were immunized with $10^7$ pfu psoralen-inactivated VSV-NJ vaccine survived both a 1 or 10 MLD VSV challenge. One of four mice that were vaccinated at $10^7$ pfu/dose psoralen-inactivated VSV-NJ survived a 100 MLD VSV challenge. The results (no. dead/no. challenged) are set forth in Table 10.

TABLE 10

Live VSV-NJ Challenge of Mice Injected with Psoralen-Inactivated VSV-NJ

| Dose Psoralen-Inactivated VSV-NJ Vaccine | Challenge Dilution | | |
|---|---|---|---|
| | $10^{-5}$ (1 MLD) | $10^{-4}$ (10 MLD) | $10^{-3}$ (100 MLD) |
| $10^7$ pfu | 0/5* | 0/5 | 3/4 |
| $10^6$ pfu | 3/5 | 4/5 | 3/6 |
| $10^5$ pfu | 5/5 | 4/5 | 7/7 |

*Number dead/number challenged

5. Virus Neutralization in Cattle Immunized with Psoralen-inactivated VSV-NJ Vaccine Four groups of six mature beef cattle each were injected with either $10^8$ or $10^7$ pfu/dose psoralen-inactivated VSV-NJ vaccine, with or without aluminum hydroxide adjuvant (1:1). Each cow was vaccinated subcutaneously (SQ) on day 0 and again on day 21. A control group consisted of an additional six cattle that were inoculated only with adjuvant on day 0 and again on day 21. All cattle were bled on days 0, 14, 21, and 35. Serum from each animal was tested for SN antibodies to VSV-NJ by standard procedures.

The aluminum hydroxide adjuvant was required to elicit significant SN titers in cattle, and $10^8$ pfu/dose induced the highest responses. The results are set forth in Table 11. A VSV-NJ virus neutralization index greater than 1000 has been reported to represent protection against $10^6$ $ID_{50}$ of live VSV by intralingual challenge in cattle. See, Castaneda et al. (1964) Proc. US Livestock San Assoc. 68:455-468.

TABLE 11

Virus Neutralization Indices* From Cattle Injected With Psoralen-Inactivated VSV-NJ Vaccine

| Group | Treatment | Animal | 0** | 14 | 21** | 35 |
|---|---|---|---|---|---|---|
| A | 10⁸ pfu/ dose + Al(OH)₃ | 310 | — | 16 | 16 | 256 |
| | | 731 | — | — | — | >16 |
| | | 911 | — | 128 | 64 | 2048 |
| | | 921 | — | 8 | 8 | 1024 |
| | | 943 | — | 16 | 32 | 1024 |
| | | 944 | — | 32 | 32 | 512 |
| B | 10⁷ pfu/ dose + Al(OH)₃ | 303 | — | — | — | 256 |
| | | 304 | — | — | — | 64 |
| | | 308 | 4 | 4 | 8 | 512 |
| | | 542 | — | — | — | 8 |
| | | 914 | — | 16 | 4 | 512 |
| | | 1670 | — | — | — | >128 |
| C | Controls | 305 | — | — | — | — |
| | | 309 | — | — | — | — |
| | | 314 | — | — | — | — |
| | | 315 | — | — | — | — |
| | | 316 | — | — | — | — |
| | | 318 | — | — | — | — |
| D | 10⁸ pfu/ dose without adjuvant | 302 | — | — | — | 4 |
| | | 611 | — | — | — | 4 |
| | | 714 | — | — | — | 8 |
| | | 732 | — | — | — | 4 |
| | | 747 | — | — | — | — |
| | | 996 | — | — | — | 32 |
| E | 10⁷ pfu/ dose without adjuvant | 101 | — | — | — | — |
| | | 312 | — | — | — | 4 |
| | | 616 | — | — | — | — |
| | | 721 | — | — | — | — |
| | | 722 | — | — | — | — |
| | | 1944 | — | — | — | — |

*Virus neutralization index is the reciprocal of the serum dilution that neturalized 32 TCID₅₀ of VSV-NJ.
**Immunization Days 6. Live VSV-NJ Challenge of Cattle Vaccinated with Psoralen-inactivated VSV-NJ Vaccine Ten mature cattle were divided into two groups of five animals each. Group I was designated experimental and Group II was designated control. All ten cattle were clinically normal and lacked evidence of previous VSV exposure; that is, they were negative for serum neutralizing (SN) antibody. Group I cattle were vaccinated subcutaneously with 10⁸ pfu (prior to inactivation) psoralen-inactivated VSV twice with a three week interval. Vaccine volume was 2 ml, containing aluminum hydroxide adjuvant. Group II cattle were not exposed to the psoralen-inactivated VSV.

Approximately two weeks post-second vaccination, the cattle of both Groups I and II were challenged intradermalingually with 0.1 ml live VSV in log dilutions of 5.6 pfu to 5.6×10⁵ pfu/injection site. Thus each animal's tongue received six separate 0.1 ml injections, representing a quantitative challenge system. Serum neutralizing titers for cattle in each group measured before and after challenge are presented in Table 12.

TABLE 12

Serum Neutralization Titers From Cattle Vaccinated With Psoralen-Inactivated VSV-NJ Vaccine

| Animal No. Day | Arrival 0 | After 1st vacc[a] 18 | After 2nd vacc[b] 35 | Day of Challenge[a] 42 | Post Challenge[c] 60 |
|---|---|---|---|---|---|
| Group I: | | | | | |
| 4009-V | neg* | 1:160 | 1:1280 | 1:1280 | 1:1280 |
| 4383-V | neg | 1:80 | 1:1280 | 1:1280 | 1:2560 |
| 4389-V | neg | 1:80 | 1:640 | 1:2560 | ND |
| 6153-V | neg | 1:80 | 1:1280 | 1:1280 | ≧1:20480 |
| 6246-V | neg | 1:320 | 1:1280 | 1:1280 | ND |
| Group II: | | | | | |
| 3780-C | neg | neg | neg | neg | 1:10240 |
| 3781-C | neg | neg | neg | neg | 1:10240 |
| 3784-C | neg | neg | neg | neg | 1:10240 |
| 4007-C | neg | neg | neg | neg | 1:10240 |
| 7912-C | neg | neg | neg | neg | 1:10240 |

[a]100 TCID₅₀ of VSV-NJ
[b]>1000 TCID₅₀ of VSV-NJ
[c]37 TCID₅₀ of VSV-NJ
*negative at 1:20, the lowest dilution tested
ND = not done Vaccinated animals had a fifty percent reduction in lesion number, and lesions on vaccinates were fifty percent smaller and healed faster than on controls. Control animals developed lesions at both earlier and later time points. On post-challenge day eighteen, all five controls had lesions whereas four of five vaccinates were normal. The fifth vaccinate's lesions were milder than those of any control animal on post-challenge day eighteen.

Using the Mann-Whitney modification of Wilcoxon's two sample test, the vaccinates were significantly protected against live VSV challenge (P=0.075). On the average, vaccinated cattle were protected against 25 times the minimum infectious dose required to produce lesions in control animals.

According to the present invention, viruses inactivated with furocoumarins and ultraviolet radiation in the substantial absence of oxygen and other oxidizing species retain their immunogenicity and are suitable as the immunogenic substance in vaccines against a number of virally-induced diseases. The inactivated viruses of the present invention are non-infectious and safe when administered to a host for vaccination, yet display enhanced antigenic integrity when compared to vaccines inactivated in the presence of oxygen.

Although the foregoing invention has been described in some detail by way of illumination and example for purposes of clarity of understanding, it will be obvious that certain changes and modifications may be practiced within the scope of the appended claims.

What is claimed is:

1. A viral vaccine produced by exposing a live virus to a preselected intensity of long wavelength ultraviolet radiation and a preselected concentration of an inactivating furocoumarin for a time period sufficiently long to render the virus non-infectious but not long enough to degrade its antigen characteristics, wherein said exposure is performed in the substantial absence of oxygen and other oxidizing species.

2. A viral vaccine as in claim 1, wherein the inactivation medium is maintained under a non-oxidizing gas atmosphere.

3. A viral vaccine as in claim 1, wherein the inactivation medium is flushed with the non-oxidizing gas.

4. A viral vaccine as in claim 2, wherein the non-oxidizing gas is selected from the group consisting of nitrogen, argon, helium, neon, carbon dioxide, and mixtures thereof.

5. A viral vaccine as in claim 1, wherein an oxygen scavenger is added to the inactivation medium.

6. A viral vaccine as in claim 5, wherein the oxygen scavenger is sodium ascorbate.

7. A viral vaccine as in claim 1, wherein the virus is exposed to the furocoumarin by adding said furocoumarin to an inactivation medium containing the live virus.

8. A viral vaccine as in claim 1, wherein the furocoumarin is introduced to the live virus by addition to a cell culture medium in which the virus is grown.

9. A viral vaccine comprising in combination: an inactivated live virus and a physiologically acceptable vaccine carrier; said virus being further characterized as inactivated by exposure to long wavelength ultraviolet radiation and an amount of a furocoumarin sufficient to inactivate the virus, which together render the virus non-infectious without destroying its antigen characteristics.

10. The vaccine in claim 9 wherein the furocoumarin is a psoralen.

11. The vaccine of claim 9 wherein the furocoumarin is 5-methoxypsoralen (5-MOP).

12. The vaccine of claim 11 wherein the furocoumarin is 8-methoxypsoralen (8MOP).

* * * * *